United States Patent [19]

Salje

[11] Patent Number: 5,459,770
[45] Date of Patent: Oct. 17, 1995

[54] X-RAY DIFFRACTOMETER

[75] Inventor: Ekhard K. H. Salje, Cambridge, England

[73] Assignee: Cambridge Surface Analytics Ltd., Cambridge, United Kingdom

[21] Appl. No.: 157,136
[22] PCT Filed: Oct. 12, 1992
[86] PCT No.: PCT/GB92/01861
 § 371 Date: Dec. 6, 1993
 § 102(e) Date: Dec. 6, 1993
[87] PCT Pub. No.: WO93/08462
 PCT Pub. Date: Apr. 29, 1993

[30] Foreign Application Priority Data

Oct. 17, 1991 [GB] United Kingdom ............. 9122085

[51] Int. Cl.[6] ............................................. G01N 23/207
[52] U.S. Cl. ......................... 378/71; 378/79; 378/81; 378/208
[58] Field of Search ........................ 378/70, 71, 79, 378/81, 73, 193, 195, 196, 208

[56] References Cited

U.S. PATENT DOCUMENTS

| | | | |
|---|---|---|---|
| 4,015,125 | 3/1977 | Donnay et al. | 378/81 X |
| 4,641,329 | 2/1987 | Green et al. | 378/79 |
| 4,658,411 | 4/1987 | Argoud et al. | 378/81 |
| 4,961,210 | 10/1990 | Fatemi | 378/81 X |
| 5,181,233 | 1/1993 | Rink et al. | 378/79 |

*Primary Examiner*—David P. Porta
*Attorney, Agent, or Firm*—Watson, Cole, Grindle & Watson

[57] ABSTRACT

An X-ray diffractometer has an X-ray source for producing an X-ray beam; a position sensitive detector for detecting diffracted X-rays over a wide angle; and means for effecting controlled relative rotation between the detector and the X-ray source incident beam. A sample holder is capable of rotation about three mutually perpendicular axes and is also capable of providing rotation of the sample relative to the sample holder about two perpendicular axes. Thin films or substrates under investigation can be individually aligned into selected diffraction geometries by such a diffractometer. The X-ray source itself may be rotatable about the axis of the X-ray beam.

8 Claims, 8 Drawing Sheets

X-RAY DIFFRACTOMETER

The present invention relates to X-ray diffractometers for use in investigation of sample such as single crystals, thin films and surfaces and the like, using position-sensitive detectors.

In GB patent application no. 8929306.2 (GB-A-2228167) the present inventor describes an X-ray diffractometer which comprises a source of X-rays for producing an incident beam falling on a sample to be investigated, a position-sensitive detector which has a wide aperture to detect the diffracted X-rays over a wide angular coverage, and means for effecting controlled relative rotation between the detector and the incident beam to increase the effective area of detection covered by the detector.

Various embodiments of the diffractometer are described and claimed.

Other prior art of interest comprises the following patent specifications: GB-A-2081440, GB-A-774572; EP-A-0207863; EP-A-0115891; and EP-A-0015475. In each of these prior patent specifications, there is shown relative movement between the X-ray source, the sample under investigation, or the detector. In EP-A-0207863 in particular, the sample is shown to be supported on a three axis stage. The position-sensitive detector is generally arcuate and the X-ray source if movable arcuately about an axis through the sample and lying in the same plane as the arc of the detector. Other art of possible relevance includes U.S. Pat. No. 3,105,901, EP-A-0165877 and *Zeitschrift fur Metallkunde* Vol. 75, no. 2, February 1984.

The present inventor has now appreciated that significant advantages are to be gained by providing additional freedoms of movement in a diffractometer of the type described and claimed in GB-A-2228167.

In accordance with a first aspect of the present invention therefore an X-ray diffractometer comprising an X-ray source for producing an X-ray beam; a position sensitive detector for detecting diffracted X-rays over a wide angle; and means for effecting controlled relative rotation between the detector and the X-ray source incident beam, is characterised by means for mounting the X-ray source for rotation about the axis of the X-ray Ream emitted therefrom.

By allowing rotation of the X-ray source so that the incident beam (which is much narrower in one dimension of the cross-section than in the other) can be arranged to lie with its longer dimension either in the arcuate plane of the detector (see GB PA 8929306.2) or perpendicular to it. By this means, in the latter orientation of the X-ray source, a thin film sample in particular, having a planar surface disposed perpendicularly to the plane of the incident beam, can be investigated in an optimum way.

According to a second aspect of the present invention, an X-ray diffractometer comprising an X-ray source for producing an X-ray beam; a position sensitive detector for detecting diffracted X-rays over a wide angle; and means for effecting controlled relative rotation between the detector and the X-ray source incident beam, is characterised by;

a sample holder capable of rotation about three mutually perpendicular axis; and means for providing rotation of the sample relative to the sample holder about two perpendicular axes, whereby thin films or substrates under investigation can be individually aligned into selected diffraction geometries.

One example of an X-ray diffractometer according to the present invention will now be described with reference to the accompanying drawings in which.

Figure 1:
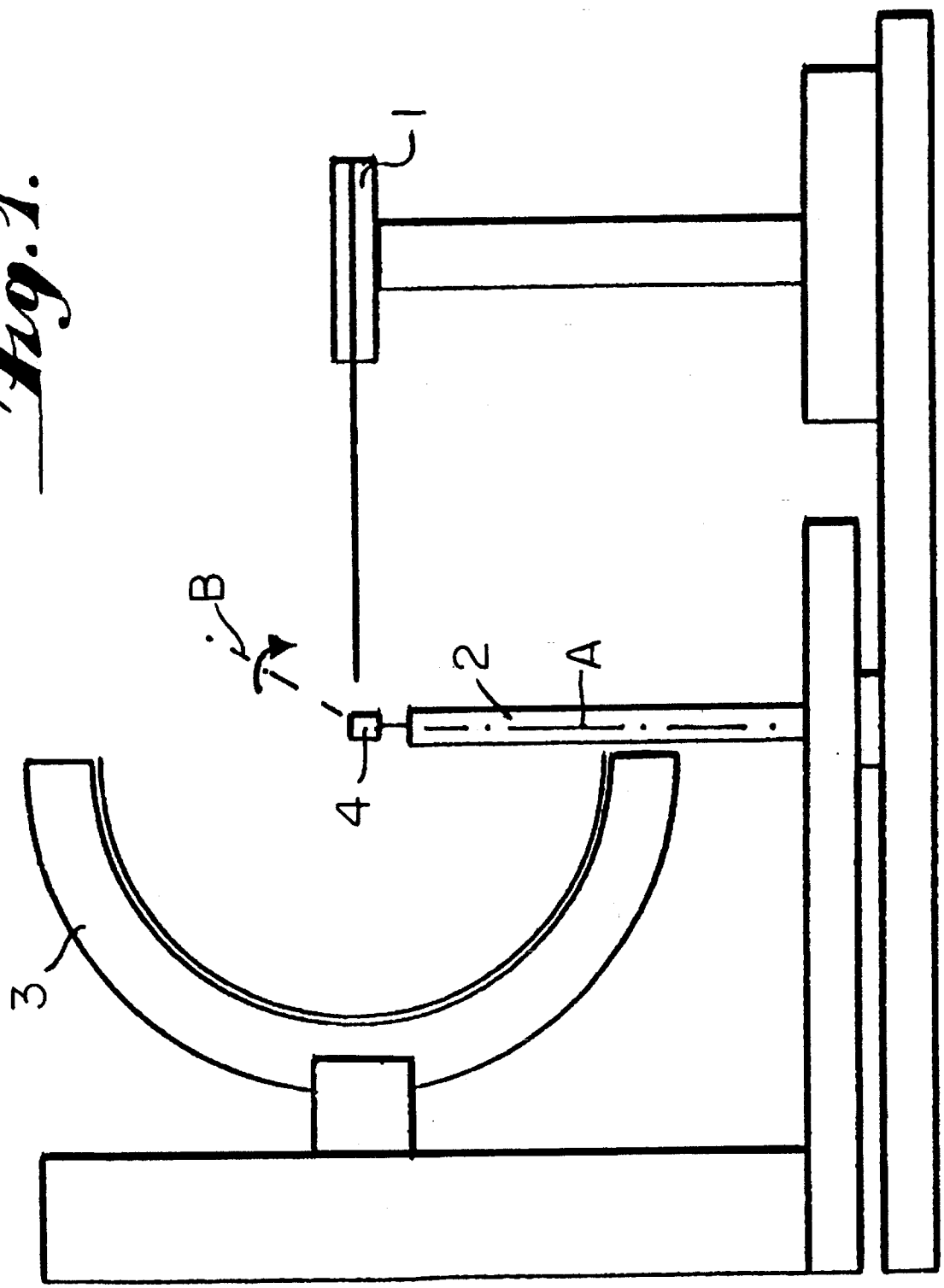
FIGS. 1 & 2 and 3 & 4 are copies of FIGS. 1 & 2 and 5 & 6 of the drawings from GB-A-2228167.
Figure 2:
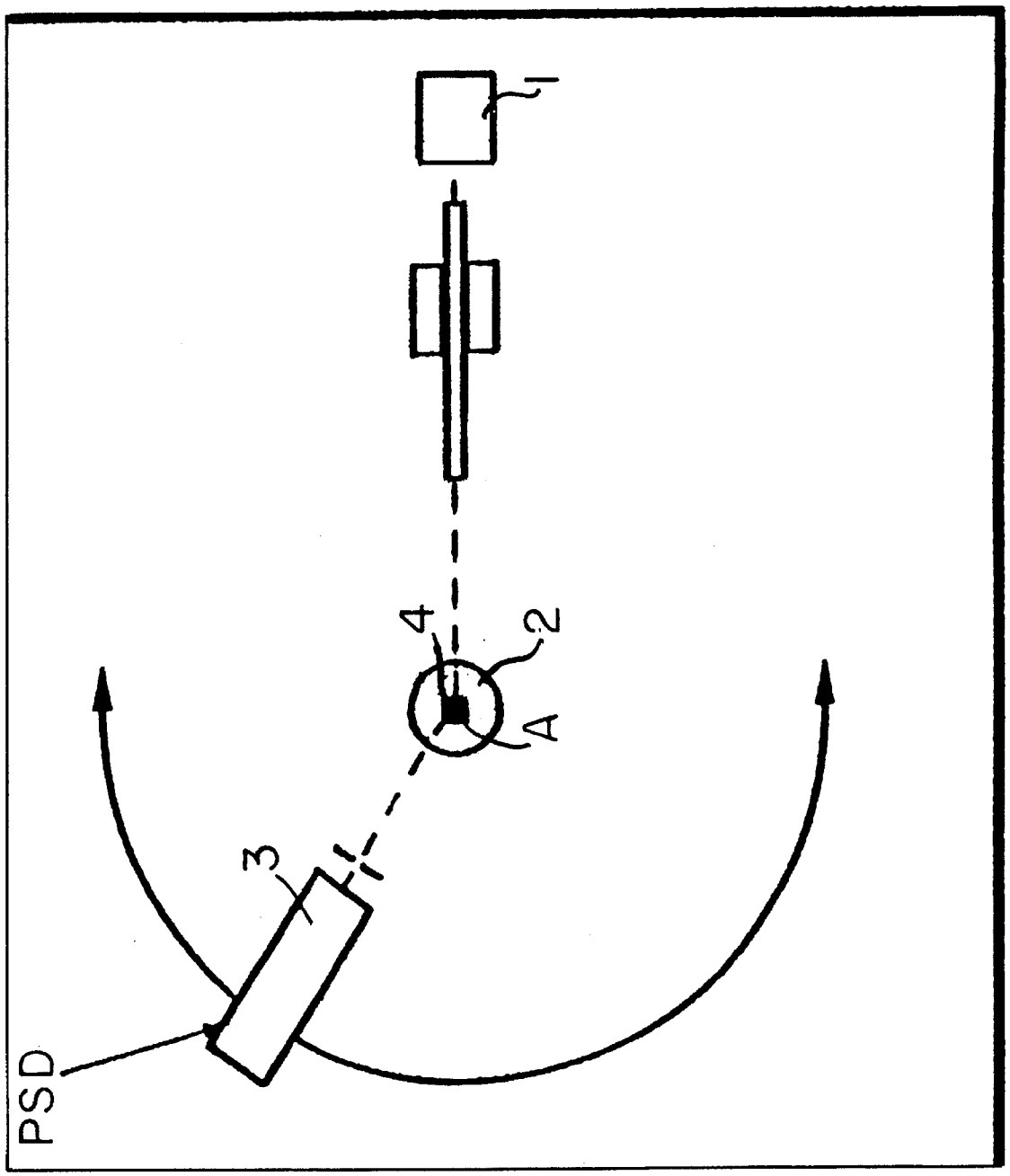

FIG. 1 illustrates the basic X-ray diffractometer described in GB patent application 8929306.2, the diffractometer comprising an X-ray source 1, a sample support 2 and an arcuate, position-sensitive X-ray detector 3. A sample, often a crystal 4, is mounted on the sample support 2 and the earlier application describes, with reference to FIGS. 2, 3 and 4 in particular, how it is possible to rotate the sample and the detector relative to one another and to the X-ray source.

In the investigation of crystalline samples, thin films etc., illumination of the sample by an X-ray beam from the X-ray source or tube 1, causes interference patterns to be generated on the surface of the detector, the detector thus being used to measure the scattering orientation and intensity of the incident X-rays.

The earlier patent application describes how the sample and detector are mounted on a common base which can be rotated around a substantially vertical axis through the sample, to obtain signals for investigation. The common axis of rotation of the sample and detector is arranged to be perpendicular to the central axis of symmetry of the detector and thus lies in the plane of the arcuate curve of the detector. The aperture of the detector is adjustable for optimising the angular resolution of the instrument and the sample can be rotated about three mutually orthogonal axis by a multi-axis motor-controlled gimbal or goniometer.

Figure 3:
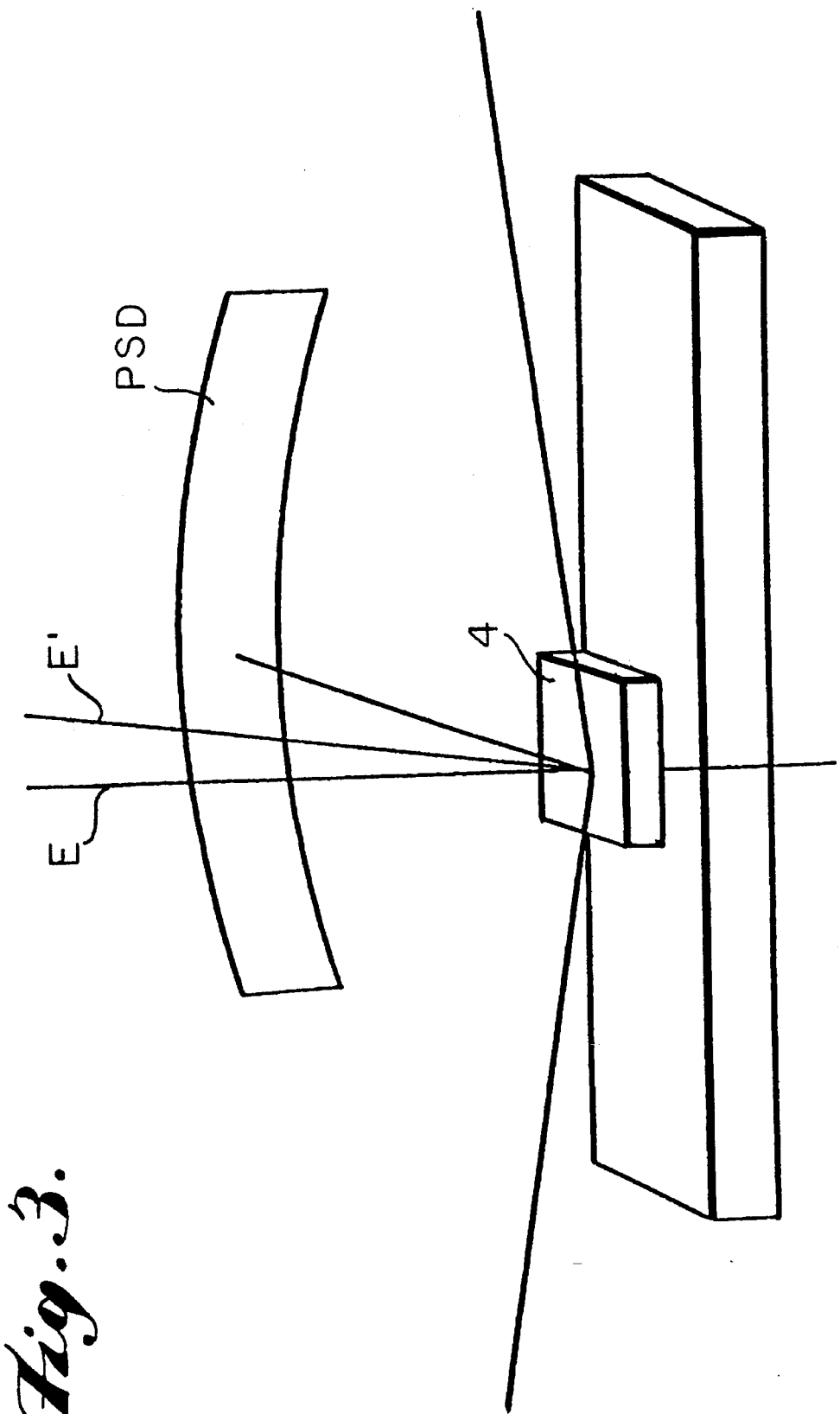
Figure 4:
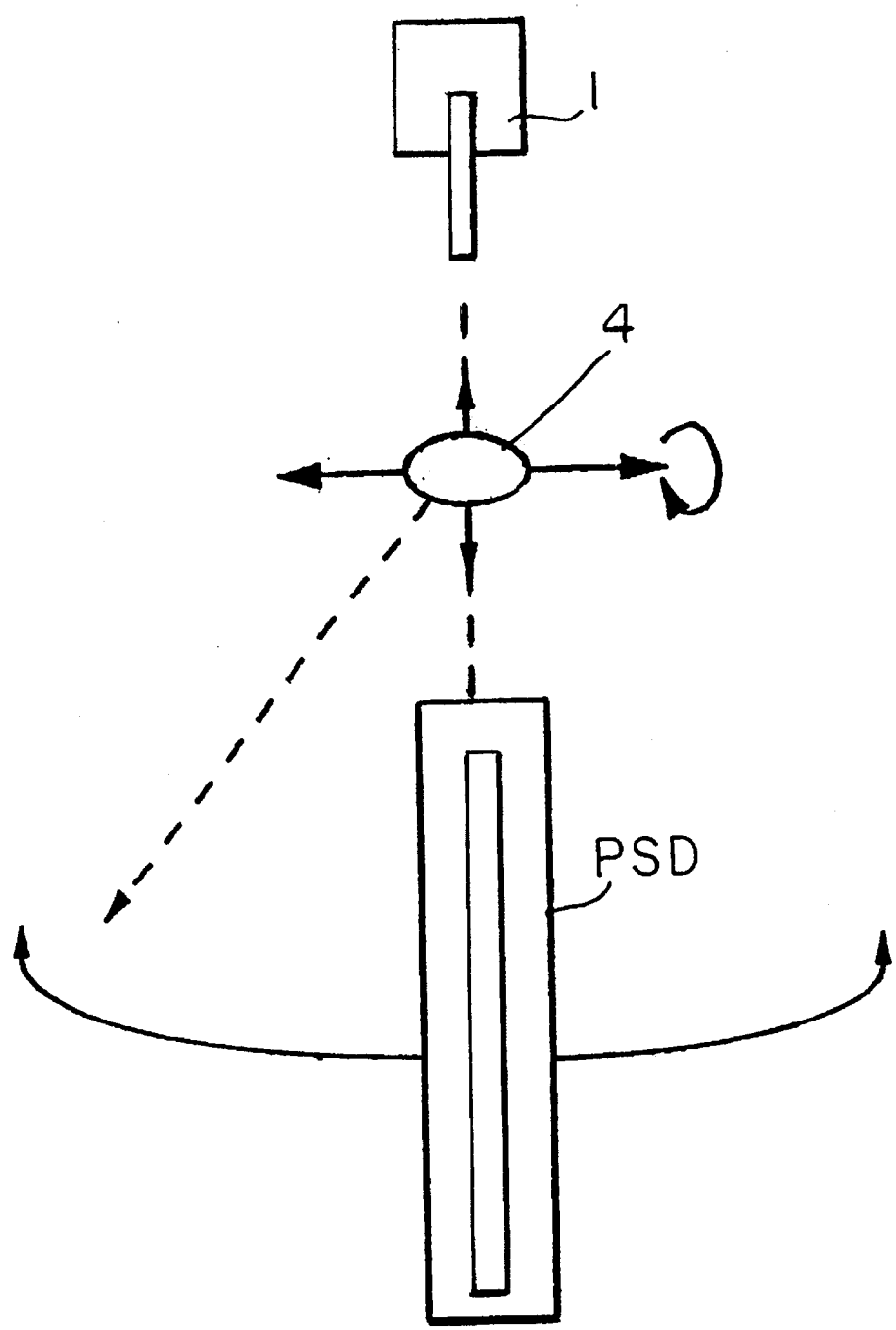
Figure 5:
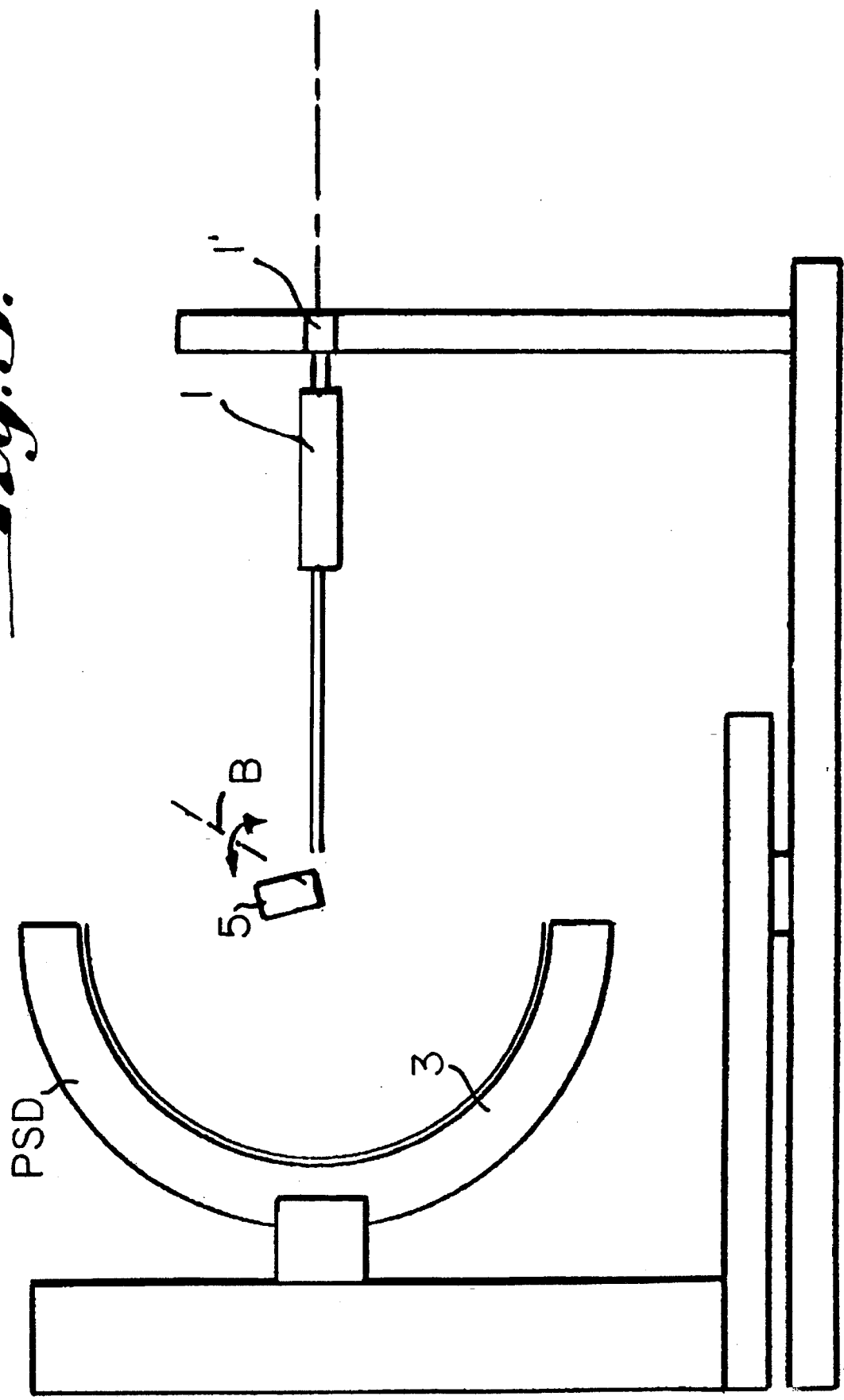
FIG. 5 is a diagrammatic side view illustrating the application of the second aspect of the present invention to the apparatus shown in GB patent application 8929306.2; and, FIGS. 6 to 9 illustrate how the first aspect of the present invention is applied to that apparatus.

FIG. 5 is a diagrammatic illustration of an example of the diffractometer of the earlier application referenced above, in which rotation of the X-ray source as desired, is provided for (and also rotation of the sample if desired), by a bearing 1', in order to provide for enhanced detection of diffracted X-rays, particularly when examining thin films and substrates. The beam of X-rays emitted by the X-ray source tube 1 has an elongate cross-section (the beam is seen face on in FIG. 5) and thus, by rotating the X-ray tube 1, the beam can be turned on its axis relative to the sample which is mounted on the bottom of the sample holder 5, the holder 5 being rotatable about three axes and therefore enabling the beam to be directed at the required angle and in the required orientation onto the sample. This is particularly important when investigating thin film samples. The holder 5 can be tilted in the gimbal assembly to any desired angle as illustrated in FIG. 3 and by reference to FIG. 7.

Figure 6:
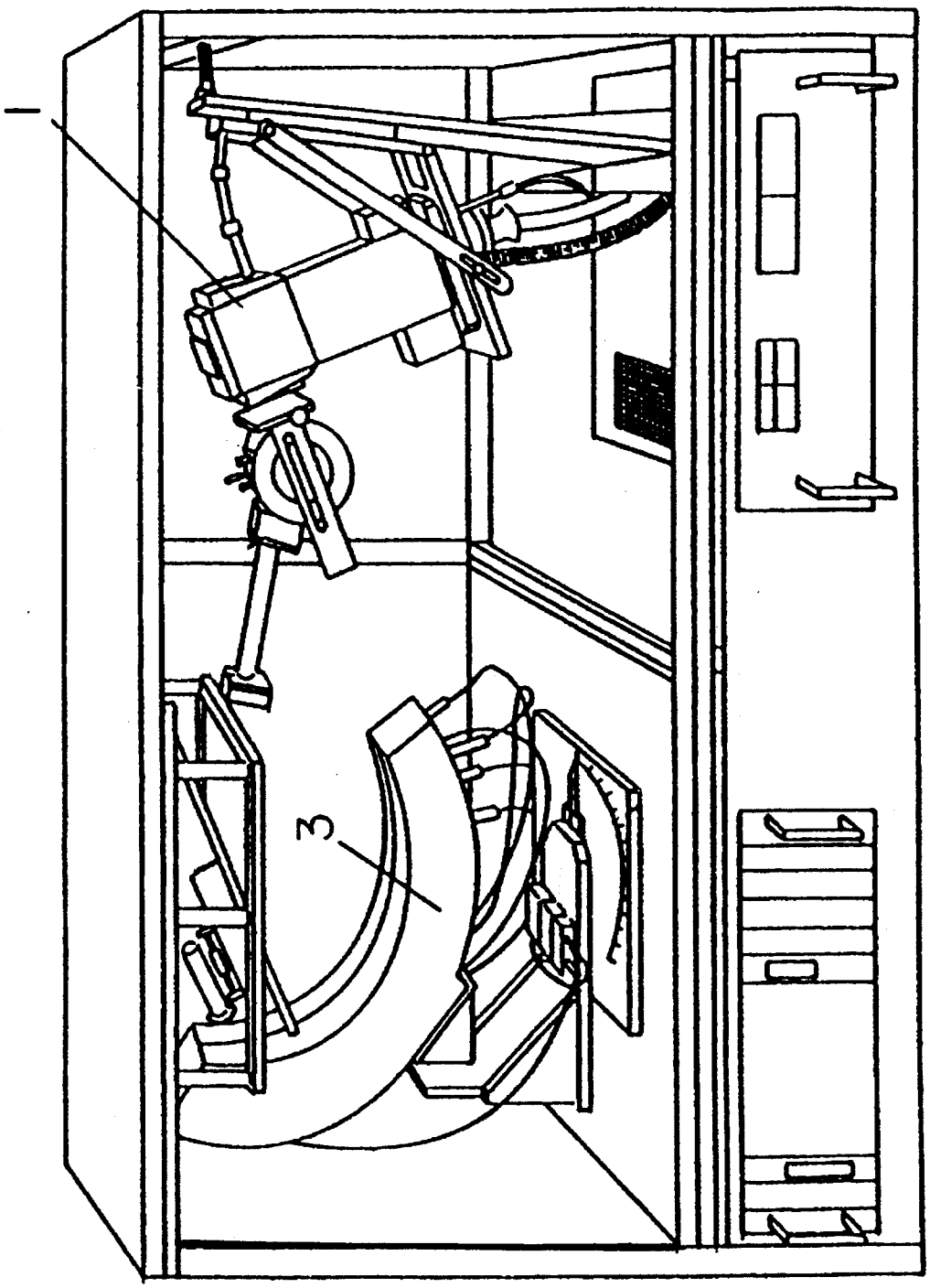
Figure 7:
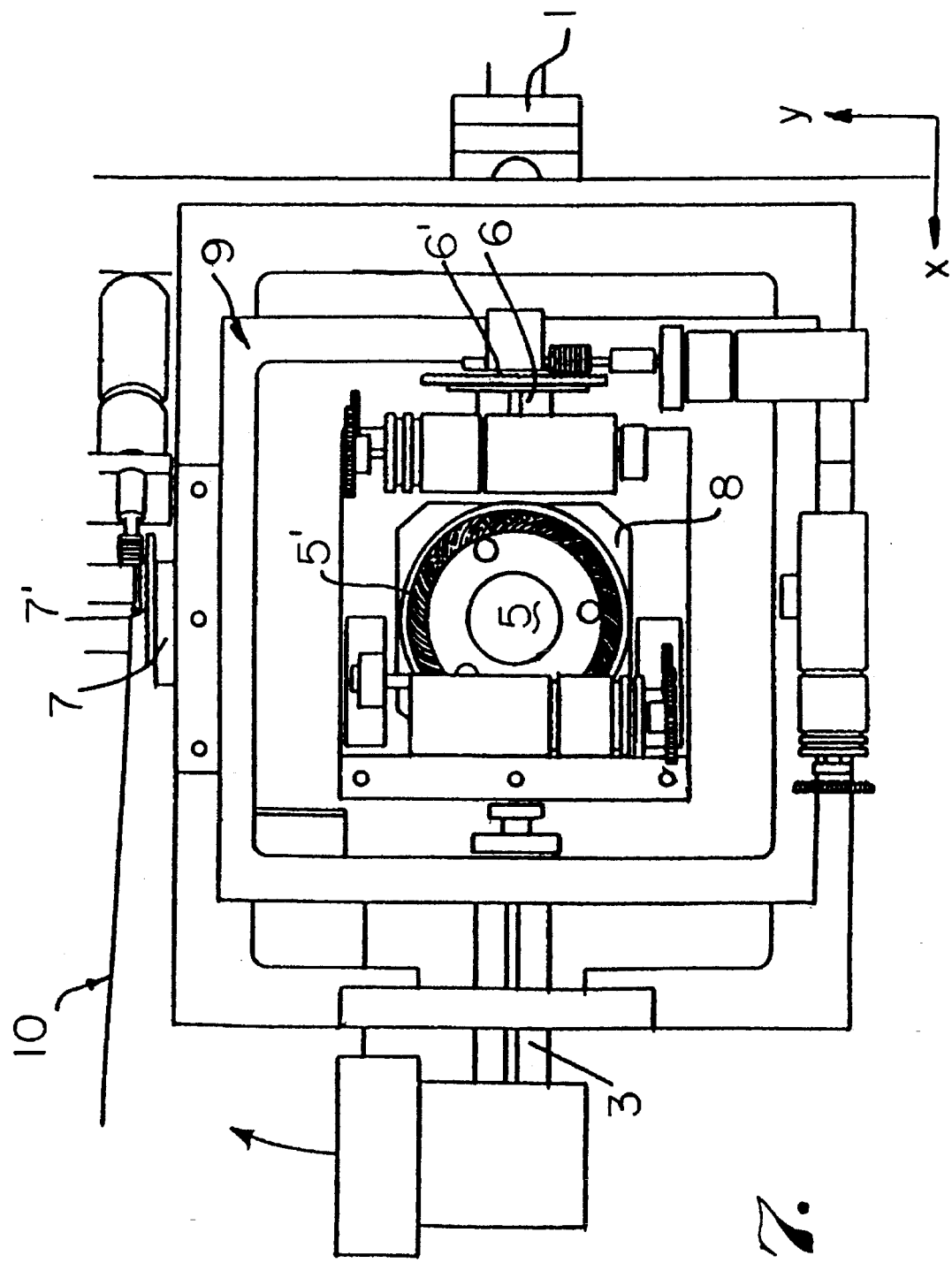

FIG. 6 is a diagrammatic perspective view of the apparatus of the invention and FIG. 7 is a plan view of the sample table area. These figures illustrate how the three mutually orthogonal axes of rotation of the sample holder may be provided in accordance with the earlier application. (Rotation of the X-ray beam about its axis is achieved by rotation of the x-y slit through which it is emitted, but, for simplicity is not shown in these figures.) FIG. 7 shows the generally cylindrical sample holder 5 with the sample attached in use to its lower planar face (see FIG. 9), the sample being rotatable about the central longitudinal axis Z—Z of the cylinder (known as the $\zeta$ movement) by a stepper motor (motor $\zeta$) driving the sample holder through a gear wheel 5', and the two other axes X—X, Y—Y of rotation of the sample table 8 being provided by gimbal bearings 6,7 and respective stepper motors (motor $\phi$, motor $\theta$), each of which gimbal bearings is normally contained in the plane of the sample table 8 which holds the sample holder 5. Relative rotational movement between the sample table 8, gimbal frame 9 and main table 10 is provided by the stepper motors driving suitable screw-threaded couplings 6',7' to provide fine adjustment.

In addition, the sample table 8 is movable translationally in the x and y directions by two further stepper motors (motor x, motor y).

Figure 8:
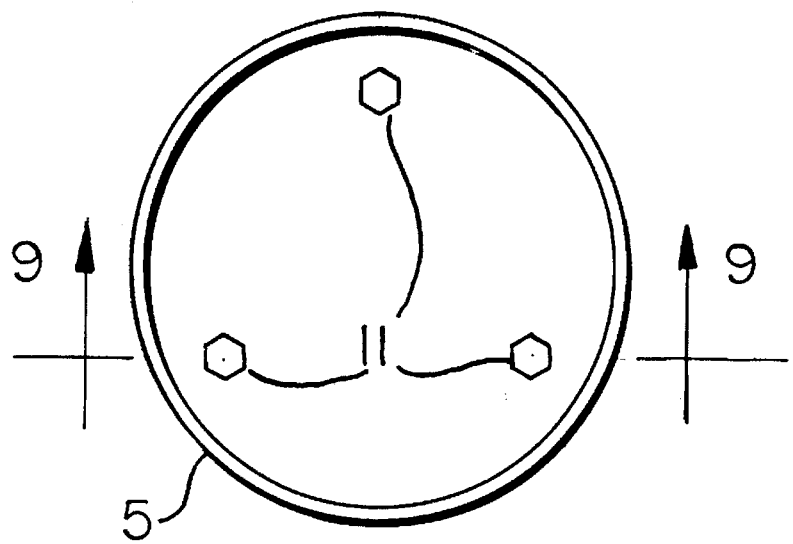
Figure 9:
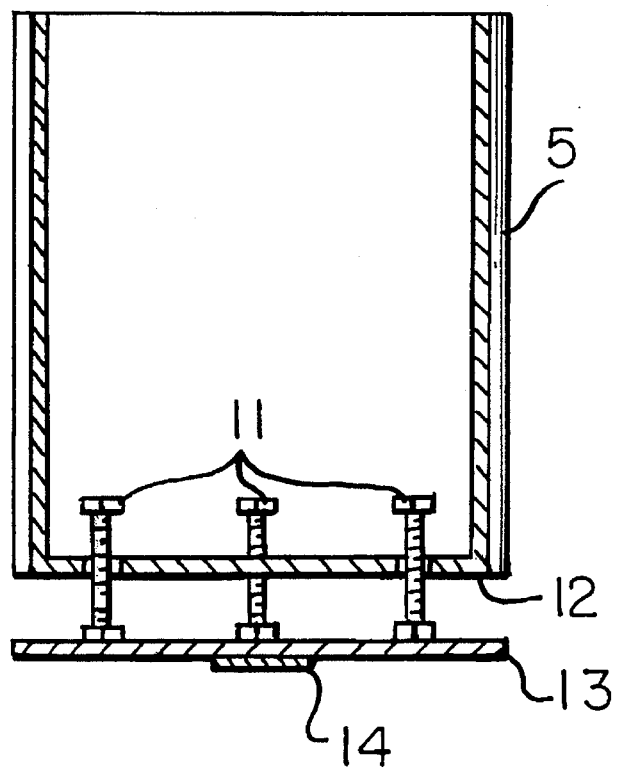

FIGS. 8 & 9 illustrate, in side section and plan view respectively, how two further axes of rotation are provided for to cater for fine adjustment of the position of the sample relative to the sample table 8. The sample holder 5 is a hollow cylinder open at its top end and carries three adjusting screws 11 which are in screw-threaded engagement with the base 12 of the cylinder 5. The adjusting screws 11 carry a sample plate 13 on which is mounted the sample 14. The adjusting screws are equiangularly disposed about the centre axis of the sample holder 5, so that adjustment of the position of the plate 13 in the two axes perpendicular to the longitudinal axis of the sample holder can be effected. Although the screws are shown as manually operated in FIG. 9, the screws could be stepper motor driven if desired.

I claim:

1. An X-ray diffractometer for investigating samples of the thin film and substrate type comprising:

an X-ray source for producing an X-ray source incident beam;

a position sensitive detector for detecting diffracted X-rays over a wide angle;

means for effecting controlled relative rotation between the detector and the x-ray source incident beam to a selected position and orientation, a sample holder capable of rotation about three mutually perpendicular axes; and means for selectively positioning the sample for irradiation in a fixed position relative to the sample holder about two perpendicular axes for individually aligning the samples under investigation into selected diffraction geometries for the corresponding thin film and substrate types.

2. A diffractometer according to claim 1, comprising: stepper motor means for effecting relative rotation between the detector and the X-ray source and rotation of the sample holder about the three mutually perpendicular axes resulting in selective rotational and translational movements thereof.

3. A diffractometer according to claim 1, wherein the sample holder (5) is rotatably supported in a sample table (8), about its axis and normal to the plane of the sample table, the sample table being gimballed about a first axis in a gimbal frame (9) which, in turn, is gimballed in a main frame (10), about a second axis at 90° to the first.

4. A diffractometer according to claim 3, further including means (x,y) for supporting the sample table for controllable translation along two perpendicular axes which lie in the plane of the sample table.

5. A diffractometer according to claim 3, wherein the sample (14) is supported on a mount (13) in the sample holder, the mount being adjustably positioned in the sample holder by means of adjustment screws (11) by means of which the position of the mount can be adjusted about a pair of axes lying in the plane of the mount.

6. A diffractometer according to comprising: stepper motor means for effecting relative rotation between the detector and the X-ray source and rotation of the sample holder about the three mutually perpendicular axes resulting in selective rotational and translational movements thereof.

7. A diffractometer according to claim 1, wherein the sample is supported on a mount in the sample holder, the mount being adjustably positioned in the sample holder by means of adjustment screws by means of which the position of the mount can be adjusted about a pair of axes lying in the plane of the mount.

8. An X-ray diffractometer comprising an X-ray source (1) for producing an X-ray beam; a position sensitive detector (3) for detecting diffracted X-rays over a wide angle; and means for effecting controlled relative rotation between the detector and the X-ray source incident beam, characterised by means (1') for mounting the X-ray source for rotation about the axis of the X-ray beam emitted therefrom.

\* \* \* \* \*